United States Patent [19]
Cauwenbergh

[11] Patent Number: 5,476,853
[45] Date of Patent: Dec. 19, 1995

[54] AGENT FOR USE AS AN ANTI-IRRITANT

[75] Inventor: Gerard F. M. J. Cauwenbergh, Vorselaar, Belgium

[73] Assignee: Janssen Pharmaceutica N.V., Belgium

[21] Appl. No.: 302,674

[22] PCT Filed: Mar. 16, 1993

[86] PCT No.: PCT/EP93/00634

§ 371 Date: Sep. 9, 1994

§ 102(e) Date: Sep. 9, 1994

[87] PCT Pub. No.: WO93/18744

PCT Pub. Date: Sep. 30, 1993

[30] Foreign Application Priority Data

Mar. 23, 1992 [EP] European Pat. Off. .............. 92200828

[51] Int. Cl.$^6$ ........................... A61K 31/495; A61K 7/42
[52] U.S. Cl. .............................. 514/253; 424/59
[58] Field of Search .................... 544/366, 370; 514/253; 424/59

[56] References Cited

U.S. PATENT DOCUMENTS

| | | | |
|---|---|---|---|
| 3,472,854 | 10/1969 | Archer | 260/268 |
| 4,011,322 | 3/1977 | Rahtz et al. | 514/253 |
| 4,250,176 | 2/1981 | Vandenberk et al. | 424/250 |
| 4,377,578 | 3/1983 | Vandenberk et al. | 544/370 |

FOREIGN PATENT DOCUMENTS 1520262  8/1978  United Kingdom .

OTHER PUBLICATIONS

Merck Manual, 15th Edition, pp. 2516–2517, 1987.

*Primary Examiner*—Cecilia Tsang
*Attorney, Agent, or Firm*—Charles J. Metz

[57] ABSTRACT

The use of a compound having the formula or a cosmetically acceptable acid addition salt form thereof, for preventing or reducing irritation or itching of the skin of human beings; cosmetic compositions comprising said agents, processes for preparing said compositions, and a method of preventing or reducing irritation or itching of the skin of human beings.

8 Claims, No Drawings

AGENT FOR USE AS AN ANTI-IRRITANT

CROSS-REFERENCE TO RELATED APPLICATION

This application is based upon PCT application Ser. No. PCT/EP 93/00634, filed Mar. 16, 1993, which claims priority from European patent application Ser. No. 92.200,828.9, filed on Mar. 23, 1992.

The present invention concerns the use of an agent as an anti-irritant, cosmetic compositions comprising said agent, processes for preparing said compositions and a method of reducing irritation of the skin.

An uneasy irritating sensation or itching feeling in the upper surface of the skin is a phenomenon affecting many people at some time, even though it does not indicate any health problem. Said irritation or itching feeling may result from having a sensitive or hypersensitive skin, e.g. in the case of a dry or broken skin, from exposure to light, insect bites, contact with irritating plants such as poison ivy, friction or contact with clothes or tissues.

The present invention is concerned with the use of a compound having the formula

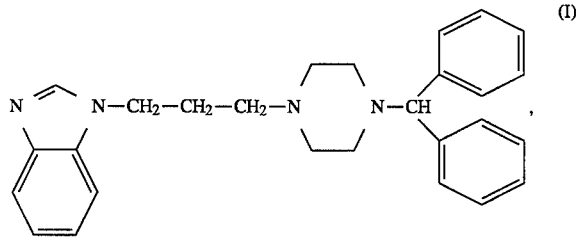

or a cosmetically acceptable acid addition salt form thereof, for preventing or reducing irritation or itching of the skin of human beings.

The present invention is also concerned with a method of preventing or reducing irritation or itching of the skin of human beings, which comprises administering topically to the skin of said human beings a compound having the formula (I) or a cosmetically acceptable acid addition salt thereof, in an amount effective in preventing or reducing the irritation or itching feeling.

The compound of formula (I), 1-[3-[4-(diphenylmethyl)-1-piperazinyl]propyl]-1H-benzimidazole is a known compound and its preparation as well as its properties are described in U.S. Pat. No. 3,472,854.

The compound of formula (I) is preferably used as such or in a cosmetically acceptable acid addition salt form. Said salt forms can conveniently be prepared by treating the base form with an appropriate acid such as, for example, hydrohalic acids, e.g. hydrochloric or hydrobromic acid; sulfuric acid; nitric acid; phosphoric acid and the like; or organic acids, such as, for example, acetic, propanoic, hydroxyacetic, 2-hydroxy-propanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. The term acid addition salt form as used hereinabove also comprises the solvates which the compound compound (I) and its acid addition salts are able to form. Examples of such solvates are, e.g. the hydrates, alcoholates and the like.

The compound of formula (I) when used in cosmetic compositions at a concentration of 0.05% to 2% (by weight based on the total weight of said cosmetic compositions), preferably 0.5% to 2%, prevents or takes away irritation or itching in the upper surface of the skin. Moreover, because of the beneficial inflammation modulating properties of compound (I), the rash and redness associated with certain instances of irritation can be prevented or diminished.

The compound (I) can be applied to the skin when necessary or convenient, e.g. at each washing occasion or thereafter; or before, during or after sunbathing. The topical administration may be repeated until a cosmetically beneficial reduction of the irritation is obtained. No special precautions are needed other then those which normally apply when using cosmetic agents.

Compound (I) is advantageously used in a micronized form, e.g. as material having an average particle size of less than 100 microns. Said micronized form has the advantage of dissolving better and more rapidly due to its high surface area, and penetrating well into the upper layers of the skin. Micronized forms of the compound (I) can be prepared following art-known micronization techniques, e.g. by milling in an appropriate mill and sieving through appropriate sieves.

The compound (I) is most preferably applied to the affected areas of the body in the form of appropriate compositions, in particular cosmetic compositions. Said compositions contain the compound (I), preferably in a 0.05 to 2% concentration (weight by weight), in particular in a 0.5% to 2% concentration, and any known dermatologically acceptable carrier and may take a wide variety of forms such as, for example, liquid forms, e.g. solutions, emulsions or suspensions in aqueous, alcoholic or oily mediums, such as toilet waters, packs, lotions, skin milks or milky lotions and shampoos; or semi-liquid formulations, e.g. creams, hydrogels, gels, pastes, ointments, salves, tinctures and the like, or solid formulations, e.g. powders.

Said preparations contain, besides the compound (I), components usually employed in such preparations. Examples of such components are oils, fats, waxes, surfactants, humectants, penetration enhancing agents, thickening agents, lipid absorbents, antioxidants, viscosity stabilizers, chelating agents, buffers, preservatives, perfumes, fragrances, dyestuffs, lower alkanols, unsaturated alcohols and the like. If desired, further active ingredients may be incorporated in the compositions, e.g. antiinflammatory agents, antibacterials, antifungals, woundhealing agents, disinfectants, vitamins, sunscreens, antibiotics or anti-dandruff agents.

The compound (I) is advantageously used in cosmetical products such as sun protecting products to be used before, during or after exposure to the sun, products for dealing with sunburnt skin, products for tanning without sun, skin-whitening products, anti-wrinkle products, daily used hygienic preparations for cleaning and caring such as soaps, shampoos, bath and shower products, shaving creams, foams or lotions, baby care products, e.g. diaper rash ointments, hygienic tissues, and products for intimate hygiene care, e.g. intimate cleansing products, and daily used cosmetic preparations such as creams, emulsions, gels, oils, lotions, skin milks, milk gels, tinted milk gels, face masks, deodorants, anti-perspirants, perfumes, toilet waters, eau de Cologne, depilatories, after-shaves, make-up articles, e.g. creams, tinted bases, powders, lipstick, cover sticks, eye-liners; products for removing make-up from the face and the eyes; hair care products, e.g. hair tints and bleaches, products for waving, straightening and fixing, setting products, cleansing products, conditioning products or hairdressing products; and the like cosmetical products.

The liquid formulations may be packaged advantageously in any dispensing device adapted for topical administration, for example in flacons, bottles or also as a spray, either using an inert compressed gas as a propellant such as nitrogen or carbon dioxide, or alternatively using a pump to provide an aerosol. Solid formulations can be applied to the skin with powder puffs or directly with a cover stick. Alternatively, solid formulations such as granules, tablets or powders may also be dissolved in baths. Semi-liquid formulations can be packaged in suitable, art-known containers such as glass, plastic or ceramic pots or tubes, e.g. PVC-covered aluminum tubes.

Other particular compositions are those wherein the compound (I) is formulated in liposome-containing compositions. Different types of liposomes may be employed such as coarse (multilayer) liposomes or unilamellar liposomes and the like, which are formed, for example, with phosphatidyl cholines, ethanolamines, serines, sphingomyelins, cardiolipins, plasmalogens, phosphatidic acids, cerebrosides and the like. The viscosity of the liposomes can be increased by addition of one or more thickening agents such as xanthan gum, hydroxypropyl cellulose, hydroxypropyl methyl cellulose and mixtures thereof. The aqueous component may consist of water optionally in admixture with electrolytes, buffers and other ingredients such as preservatives. Preferred electrolytes are calcium, sodium and potassium chloride. The organic component may consist of a solvent such as ethanol, glycerol, propylene glycol, a polyethylene glycol and a suitable phospholipid such as, lecithin, phosphatidyl choline, phosphatidyl ethanolamine, phosphatidyl serine, phosphatidyl inositol, lysophosphatidyl choline, phosphatidyl glycerol and the like. Other lipophilic additives which may be added to selectively modify the characteristics of the liposomes are, e.g. stearylamine, phosphatidic acid, tocopherol, cholesterol, lanolin and the like.

For preparing ointments, creams, toilet waters, skin milks, and the like, compound (I) is combined in intimate admixture with a cosmetically acceptable carrier. In ointments or creams, the carrier for example consists of 1 to 20%, in particular 5 to 15% of a humectant, 0.1 to 10%, in particular from 0.5 to 5% of a thickener, and water, or said carrier may consist of 70 to 99%, in particular 80 to 95% of a surfactant, and 0 to 20%, in particular 2.5 to 15% of a fat; or 80 to 99.9%, in particular 90 to 99% of a thickener; or 5 to 15% of a surfactant, 2–15% of a humectant, 0 to 80% of an oil, very small (0% to <2%) amounts of preservative, colouring agent and/or perfume, and water. In a toilet water, the carrier for example consists of 2 to 10% of a lower alcohol, 0.1 to 10% or in particular 0.5 to 1% of a surfactant, 1 to 20%, in particular 3 to 7% of a humectant, 0 to 5% of a buffer, water and small amounts (0% to <2%) of preservative, dyestuff and/or perfume. In a milk gel, the carrier typically consists of 50 to 80% of water, preferably 70 to 80% of water; 8 to 20%, preferably 10 to 15% of an alcohol; 1 to 10%, preferably 2 to 5% of a surfactant; 0.5 to 2% of one or more thickeners; and 0 to 3% of preservatives, humectants, nutritional factors, vitamins, astringents and/or perfumes. Other active ingredients may be incorporated at doses ranging from 0.005% to 0.5%, particularly from 0.01% to 0.1%. Preferably the above formulations have a pH ranging from 5 to 7.5, particularly from 5.5 to 7. Said pH can be established by the addition of a base, e.g. sodium hydroxide, or an acid, e.g. lactic, citric or phosphoric acid, or a buffer, e.g. a citrate, phosphate, lactate or acetate buffer.

Typical anti-irritant sun protecting formulations may comprise the active ingredient (I) at the concentrations mentioned hereinabove; water, one or more sunscreening agents such as, for example, physical sunscreens, e.g. zinc oxide, titanium oxide, calcium carbonate, magnesium oxide, kaolin, talc, or chemical sunscreens, e.g. aminobenzoates, benzophenones, camphor derivatives, cinnamates, salicylates, anthranilates phenylbenzimidazole sulphonic acid, butyl methoxydibenzoyl methane and the like, at an effective and tolerable concentration, e.g. between 0.1% and 15%; one or more non-polar ingredients such as, for example, mineral oil, silicone fluids, e.g. dimethicone, coconut oil, isopropyl myristate, isopropyl isostearate, glycerin myristate, octyl octanoate, benzoates and the like, each at a concentration ranging from about 0.5% to 15%, particularly from 1% to 10%; one or more thickening agents, e.g. stearyl alcohol; one or more surfactants, e.g. potassium cetyl phosphate at a concentration ranging from about 0.5% to 9%, preferably from 1% to 5%; one or more emulsifiers, e.g. glyceryl stearate, polyethylene glycol stearate, ethoxylated fatty alcohols, e.g ceteareth, steareth and the like at a concentration of 0.1% to 10%; one or more suspending agents such as, for example magnesium aluminum silicate or a carboxyvinylpolymer at a concentration of 0.1% to 3%; one or more dispersing agents, e.g. polyvinylpyrrolidinone/eicosene copolymer, at a concentration of 0.5% to 10%; one or more humectants such as, for example, glycerin, propylene glycol, sorbitol and similar alcohols at a concentration of 0.1% to 10%. Said formulations may further comprise vitamins such as, for example, vitamin E (tocopherol) and derivatives, e.g. tocopheryl acetate, panthenol and the like, at a concentration of 0.1% to 5%; and optionally preservatives, e.g. phenoxyethanol, in an amount sufficient to prevent the degradation of the final composition; fragrances at a concentration of 0% to 2%, preferably 0.1% to 1%; and acid, base or buffer in an amount sufficient to give an appropriate pH to the final composition.

In the aforementioned preparations, all % symbols refer to weight by weight percentage. The humectant, surfactant, oil, other active ingredient, etc. referred to in said preparations may be any such component used in the cosmetic arts. Further, when in the above compositions one or more of the components make up the major part of the composition, the other ingredients can evidently be not present at their indicated maximum concentration and therefore will make up the remainder of the composition.

Experimental Part

Example I: Preparation of Compound (I)

a) To a stirred mixture of 35 g of 1H-benzimidazole in 175 ml of a sodium hydroxide solution 2N were added dropwise 31.5 ml of 3-bromo-1-propanol. Upon completion, stirring was continued for 2 hours at reflux temperature. After cooling, the product was extracted with dichloromethane and the extract was dried, filtered and evaporated, yielding 47 g (89%) of 3-(1H-benzimidazole)-1-propanol.

b) To a stirred solution of 17.6 g of 3-(1H-benzimidazole)-1-propanol in 151 ml of trichloromethane were added dropwise 8.9 ml of thionyl chloride. Upon completion, stirring was continued for 2 hours at reflux temperature. The reaction mixture was evaporated and crushed ice was added to the residue. The whole was neutralized with a diluted sodium hydroxide solution and the product was extracted with dichloromethane. The extract was dried, filtered and evaporated. The residue was purified by column chromatography (silica gel; $CHCl_3/CH_3OH$ 95:5). The eluent of the desired fractions were collected and evaporated, yielding 9 g (46%) of 1-(3-chloropropyl)1H-benzimidazole.

c) A mixture of 4.5 g of 1-(3-chloropropyl)-1H-benzimidazole, 5.1 g of 1-(diphenylmethyl)piperazine, 3.7 g of sodium carbonate, 0.1 g of potassium iodide and 100 ml of 4-methyl-2-pentanone was stirred overnight at reflux temperature. After cooling, there was added water and the reaction mixture was separated. The organic layer was dried, filtered and evaporated. The residue was purified by column chromatography (silica gel; CHCl$_3$/CH$_3$OH 95:5). The eluent of the desired fraction was evaporated and the residue was crystallized from a mixture of 4-methyl-2-pentanone and 2,2'-oxybispropane. The product was filtered off and dried, yielding 1.5 g (14.5%) of 1-[3-[4-(diphenylmethyl)-1-piperazinyl]propyl]-1H-benzimidazole; mp. 132.3° C.

Example 2: Alternative Preparation of Compound (I)

a) To a mixture of 20 g of 1H-benzimidazole in 420 ml of 2-butanone there were added 28.4 g of potassium hydroxide flakes and the mixture was stirred for half an hour at room temperature. 80.6 g of 1-bromo-3-chloropropane were added and the reaction mixture was stirred for two more hours at room temperature. 250 ml of water were added and the organic layer was separated. To the organic layer there were added 250 ml of water and the reaction mixture was acidified with concentrated hydrochloric acid to pH 2–3. The aqueous layer was separated, extracted with 100 ml of dichloromethane and then 250 ml of 4-methyl-2-pentanone were added. The bilayered system was basified with a 50% (w/w) sodium hydroxide solution to pH 9–10 and the organic layer was separated, dried, and used as such in the following reaction step.

b) To the solution obtained in the previous step there were added 38 g of 1-(diphenylmethyl)piperazine and 21.2 g of sodium carbonate. The reaction mixture was heated to reflux for 24 hours. After cooling to ambient temperature, the reaction mixture was poured into water. The organic layer was separated and acidified with isopropanol saturated with hydrochloric acid. Upon stirring the resulting solution for 30 minutes, crystallization ensued. The reaction was further acidified with isopropanol saturated with hydrochloric acid and stirred. The precipitate was filtered off, washed with 4-methyl-2-pentanone and dried in vacuo at 50° C., yielding 44.2 g (65.5%) of 1-[3-[4-(diphenylmethyl)]-1-piperazinyl]propyl]-1H-benzimidazole hydrochloride.

c) 44.2 g of the hydrochloride salt obtained in the previous step were dissolved in 77.6 ml of water and 155.2 ml of dichloromethane were added thereto. While vigorously stirring the thus obtained mixture, there were added dropwise 7.8 ml of ammonia and the vigorous stirring was continued for two hours. The organic layer was separated, dried, filtered and evaporated, thus yielding 39.4 g (89.1%) of 1-[3-[4-(diphenylmethyl)-1-piperazinyl] propyl]-1H-benzimidazole; mp. 133.7° C.

Composition Examples

The following formulations exemplify typical compositions in accordance with the present invention.

"Active ingredient" (A.I.) as used throughout these examples relates to a compound of formula (I) or a cosmetically acceptable acid addition salt thereof.

Example 3: 0.5% Cream 75 mg stearyl alcohol, 2 mg cetyl alcohol, 20 mg sorbitan monostearate and 10 mg isopropyl myristate are introduced into a doublewall jacketed vessel and heated until the mixture has completely molten. This mixture is added to a separately prepared mixture of purified water, 200 mg propylene glycol and 15 mg polysorbate 60 having a temperature of 70° to 75° C. while using a homogenizer for liquids. The resulting emulsion is allowed to cool to below 25° C. while continuously mixing. A solution of 5 mg A.I., 1 mg polysorbate 80 and purified water and a solution of 2 mg sodium sulfite anhydrous in purified water are next added to the emulsion while continuously mixing. The cream is homogenized and filled into suitable tubes.

Example 4: 1% Liposome Formulation

A mixture of 1 g A.I. microfine, 20 g phosphatidyl choline, 5 g cholesterol and 10 g ethyl alcohol is stirred and heated at 55°–60° C. until complete dissolution and is added to a solution of 0.2 g methyl paraben, 0.02 g propyl paraben, 0.15 g disodium edetate and 0.3 g sodium chloride in purified water while homogenizing. 0.15 g Hydroxypropylmethylcellulose in purified water ad 100 g is added and the mixing is continued until swelling is complete.

Example 5: 0.5% Liposome Formulation

A mixture of 10 g phosphatidyl choline and 1 g cholesterol in 7.5 g ethyl alcohol is stirred and heated at 40° C. until complete dissolution. 0.5 g A.I. microfine is dissolved in purified water by mixing while heating at 40° C. The alcoholic solution is added slowly to the aqueous solution while homogenizing during 10 minutes. 1.5 g Hydroxypropylmethylcellulose in purified water is added while mixing until swelling is complete. The resulting solution is adjusted to pH 5.0 with sodium hydroxide 1 N and diluted with the rest of the purified water ad 100 g.

I claim:

1. A method for preventing or treating irritation or itching of the skin, which comprises the topical administration to the skin of a composition containing, as an active ingredient, an effective amount of 1-[3-[4-(diphenylmethyl)-1-piperazinyl]propyl]-1H-benzimidazole or a cosmetically acceptable acid addition salt thereof.

2. The method of claim 1 wherein said composition contains 0.05% to 2% of the active ingredient by weight based on the total weight of the composition.

3. The method of claim 1 wherein said composition further comprises liposomes.

4. A method for protecting the skin from sun damage which comprises the topical administration to the skin either before, during or after exposure to the sun of a composition containing, as an active ingredient, an effective amount of 1-[3-[4-(diphenylmethyl)- 1-piperazinyl]propyl]-1H-benzimidazole or a cosmetically acceptable acid addition salt thereof.

5. The method of claim 4 wherein said composition further comprises one or more sunscreening agents and 0.05% to 2% of the active ingredient by weight based on the total weight of the composition.

6. The method of claim 4 wherein said composition further comprises liposomes.

7. The method of claim 5 wherein said composition comprises one or more sunscreening agents selected from the group consisting of titanium oxide, a camphor derivative, a cinnamate, a benzophenone, phenylbenzimidazole sulfonic acid and butyl methoxydibenzoyl methane.

8. The method of claim 6 wherein said composition comprises one or more sunscreening agents selected from the group consisting of titanium oxide, a camphor derivative, a cinnamate, a benzophenone, phenylbenzimidazole sulfonic acid and butyl methoxydibenzoyl methane.

* * * * *